US011203769B1

(12) United States Patent
Chakrabarti et al.

(10) Patent No.: US 11,203,769 B1
(45) Date of Patent: Dec. 21, 2021

(54) HYDROGEN PEROXIDE AND GLUCONIC ACID PRODUCTION

(71) Applicants: Gaurab Chakrabarti, Dallas, TX (US); Sean T. Hunt, Dallas, TX (US)

(72) Inventors: Gaurab Chakrabarti, Dallas, TX (US); Sean T. Hunt, Dallas, TX (US)

(73) Assignee: SOLUGEN, INC.

( * ) Notice: Subject to any disclaimer, the term of this patent is extended or adjusted under 35 U.S.C. 154(b) by 38 days.

(21) Appl. No.: 15/430,782

(22) Filed: Feb. 13, 2017

(51) Int. Cl.
| | |
|---|---|
| *C12P 7/58* | (2006.01) |
| *C01B 15/022* | (2006.01) |
| *C07H 3/02* | (2006.01) |
| *C12N 9/04* | (2006.01) |
| *C12M 1/40* | (2006.01) |
| *C12M 1/00* | (2006.01) |
| *C12P 3/00* | (2006.01) |

(52) U.S. Cl.
CPC .............. *C12P 7/58* (2013.01); *C01B 15/022* (2013.01); *C07H 3/02* (2013.01); *C12M 21/18* (2013.01); *C12M 29/02* (2013.01); *C12M 47/10* (2013.01); *C12N 9/0006* (2013.01); *C12P 3/00* (2013.01); *C12Y 101/03004* (2013.01)

(58) Field of Classification Search
CPC . C12P 7/58; C12P 3/00; C01B 15/022; C07H 3/02; C12M 21/18; C12M 29/02; C12N 9/0006; C12Y 101/03004
See application file for complete search history.

(56) References Cited

U.S. PATENT DOCUMENTS

| | | | | |
|---|---|---|---|---|
| 2,990,341 | A * | 6/1961 | Graybill | C01B 15/013 203/12 |
| 3,619,396 | A * | 11/1971 | Walon | B01D 61/44 204/522 |
| 3,935,071 | A | 1/1976 | Bergmeyer et al. | |
| 4,920,055 | A | 4/1990 | Hoiberg et al. | |
| 5,288,746 | A | 2/1994 | Pramod | |
| 5,712,259 | A | 1/1998 | Birkmayer | |
| 6,274,114 | B1 | 8/2001 | Ledon et al. | |
| 6,500,649 | B2 | 12/2002 | Fouache et al. | |
| 6,712,949 | B2 | 3/2004 | Gopal | |
| 6,828,130 | B2 * | 12/2004 | Chatterjee | C12P 7/58 435/137 |
| 2005/0266290 | A1 * | 12/2005 | Sun | B82Y 5/00 429/401 |
| 2006/0252947 | A1 * | 11/2006 | Haas | C07D 301/12 549/531 |
| 2009/0030194 | A1 | 1/2009 | Hamayasu et al. | |
| 2014/0234202 | A1 | 8/2014 | Vandenbussche et al. | |
| 2014/0377798 | A1 | 12/2014 | Ertl et al. | |
| 2015/0030505 | A1 | 1/2015 | Bloomfield et al. | |
| 2016/0264511 | A1 * | 9/2016 | Wonders | B01J 19/006 |

FOREIGN PATENT DOCUMENTS

| | | |
|---|---|---|
| CN | 1188114 A | 1/1998 |
| CN | 103708426 A | 4/2014 |
| EP | 0745677 B1 | 4/2002 |

OTHER PUBLICATIONS

Manley, Dextrose Equivalence, Technology of Biscuits, Crackers and Cookies (Third Edition) 2000.*
Gas-Solid Separations (Chapter 20) jpgs. 691-716, 2010.*
Godjevargova et al., Gluconic Acid Production in Bioreactor with Immobilized Glucose Oxidaase Plus Catalase on Polymer Membrane Adjacent to Anion-Exchange Membrane, Macromol. Biosci. 2004, 4, 950-956.*
Nishiwaki et al. Bioprocess Engineer. (1995) 12: 109-114 (Year: 1995).*
Tomotani et al. Appl. Biochem. Biotechnol. (2005) 121-124:149-162 (Year: 2005).*
Nakao et al. Chem. Engineer. Sci. (1997) 52(21-22) 4127-4133 (Year: 1997).*
Deed, Terry, "The Manufacture of Hydrogen Peroxide," New Zealand <retrieved on Oct. 15, 2015 from the web at: http://nzic.org.nz/ChemProcesses/production/1E.pdf>.
Kleppe, Kjell, "The Effect of Hydrogen Peroxide on Glucose Oxidase from Aspergillus niger," Biochemistry, Jan. 1966, vol. 5, No. 1, pp. 139-143.

* cited by examiner

*Primary Examiner* — Susan M Hanley
(74) *Attorney, Agent, or Firm* — Law Office of Sam Sokhansanj PLLC

(57) ABSTRACT

A hydrogen peroxide and gluconic acid production method and system is disclosed that can include receiving an aqueous solution having glucose, water, and glucose oxidase at a reaction chamber. Here, the reaction chamber facilitates an enzymatic reaction between a gas phase and a liquid phase of the aqueous solution, thereby yielding a first solution comprising hydrogen peroxide, gluconic acid, and the glucose oxidase. The method can further include receiving the first solution at a separation chamber, wherein the separation chamber is comprised of a semi-permeable membrane having a pre-defined molecular weight barrier for separating the glucose oxidase, thereby resulting in a combined hydrogen peroxide and gluconic acid solution. The method can further include at least partially converting the gluconic acid into a gluconate salt, and separating and concentrating the hydrogen peroxide from the gluconic acid or gluconate salt via vacuum flash evaporation and vacuum distillation.

18 Claims, 12 Drawing Sheets

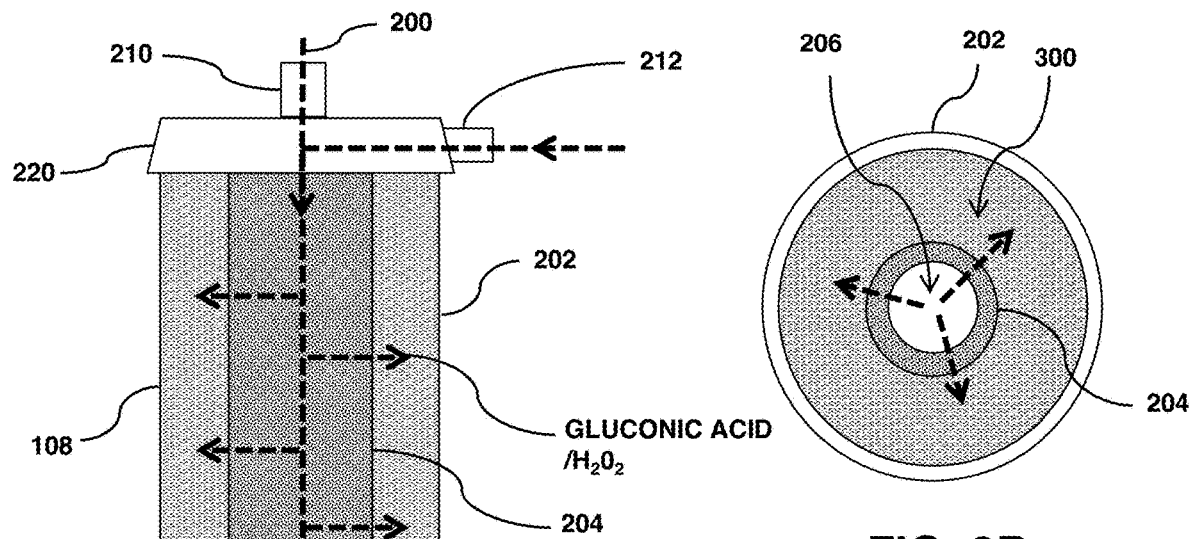
FIG. 3B
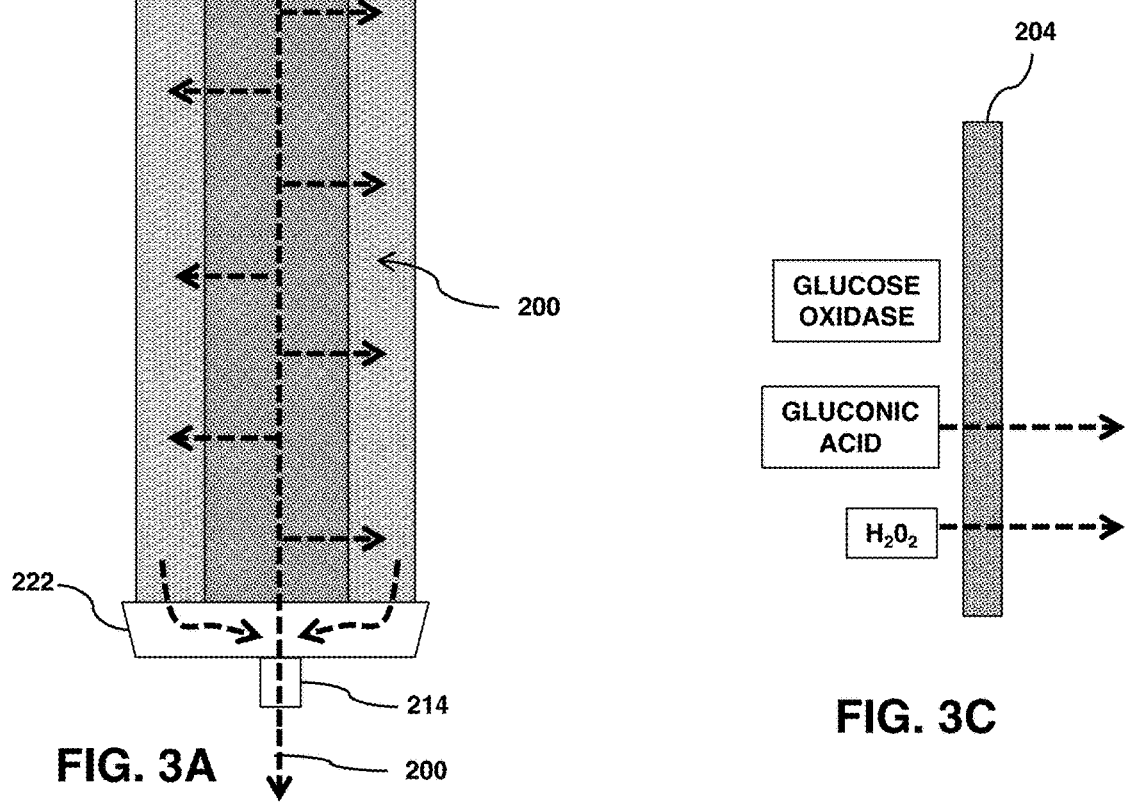
FIG. 3A
FIG. 3C

HYDROGEN PEROXIDE AND GLUCONIC ACID PRODUCTION

BACKGROUND

This section is intended to introduce the reader to aspects of art that may be related to various aspects of the present disclosure described herein, which are described and/or claimed below. This discussion is believed to be helpful in providing the reader with background information to facilitate a better understanding of the various aspects of the present disclosure described herein. Accordingly, it should be understood that these statements are to be read in this light, and not as admissions of prior art.

Industrial synthesis of hydrogen peroxide is predominantly achieved by using the Riedel-Pfleiderer process that uses the autoxidation of a 2-alkylanthrahydroquinone compound to the corresponding 2-alkylanthraquinone, which results in the formation of hydrogen peroxide. In particular, the hydrogen peroxide is typically produced using a cyclical anthraquinone process (AO-process) comprising the hydrogenation of anthraquinone working solution in a catalytic reactor and the oxidation of the hydrogenated anthraquinone working solution by air in a multi-stage packed bed or sieve plate tower while simultaneously producing hydrogen peroxide in the organic stream, with the consecutive extraction of the hydrogen peroxide from the anthraquinone working solution by water in a multistage counter-current extraction column process. The organic solvent of choice is typically a mixture of two types of solvents, one being a good solvent of the quinone derivative (usually a mixture of aromatic compounds) and the other being a good solvent of the hydroxyquinone derivative (usually a long chain alcohol or cyclic ester). In addition to the main AO-process steps, there may be other ancillary process steps involved, such as the separation of the hydrogenation catalyst from the working solution; the recovery and polish purification of the anthraquinone working solution, the accompanying solvents, their recycle to the hydrogenator, and the recovery, polish purification and stabilization of the hydrogen peroxide product.

Accordingly, the conventional AO-processes and respective production plants are complicated and require many and large installments of equipment, several competent staff for maintenance of the equipment and operation of the main and ancillary process steps, and special safeguards to handle the resulting hydrogen peroxide in its usually high concentrations of 40 percent, and further distilled to concentrations of 50 to 70 percent. Hence, much management attention and frequent maintenance is required. Although one might assume that the AO-process may be performed on small-to medium-scale so as to merely satisfy local demand, in the state of the art it is still deemed that such processes require the use of many pieces of equipment, much management attention, and frequent maintenance, and that they are difficult to scale down and difficult to make such processes profitable.

In addition, the conversion of glucose into gluconic acid is also of great interest for many technical, industrial, medical, and consumer related purposes. The problem is usually related to the separation and removal of glucose from mixtures thereof with other substances, especially with other sugars, such as fructose, or the preparation of gluconic acid. The separation of glucose is a special problem, for example, in the case of sugars, which still contain small amounts of glucose, which are very difficult to remove. It is generally known that glucose can be converted into gluconic acid by oxidation with oxygen in an aqueous solution, with the catalytic action of the enzyme glucose oxidase. However, the current conventional process is not suitable for large-scale use because glucose oxidase quickly loses its activity during the reaction process. Conventionally, these difficulties had been overcome by binding glucose oxidase to an insoluble carrier. However, it has been found that, in practice, this cannot be carried out efficiently because although the carrier-bound glucose oxidase can be separated, it is inactivated in a very short period of time by hydrogen peroxide as a by-product of the reaction of glucose with glucose oxidase. Various other measures have been proposed to overcome this, such as introducing other elements/additives into the reaction process, namely, metals such as palladium or ruthenium. However, the introduction of other elements/additives into the reaction process can reduce the amount of hydrogen peroxide and/or gluconic acid in the final product, in addition to introducing unwanted additives.

Hence, current conventional methods have not been able to produce a combination of both gluconic acid and hydrogen peroxide in the final product solution that have at least 0.1% wt. hydrogen peroxide and at least 0.1% wt. gluconic acid in the final product. Specifically, conventional methods have resulted in either the two following scenarios: (a) a very high amount gluconic acid and trace amount of hydrogen peroxide concentrations, or (b) trace amounts of both gluconic acid and hydrogen peroxide concentrations. In addition, such conventional methods have required equipment and systems on a large scale that have not been economically feasible on small scales, similar to the conventional large scale methods of hydrogen peroxide production as previously discussed.

Therefore, a simple process is needed for converting glucose to both gluconic acid and hydrogen peroxide in the presence of glucose oxidase but without the above-mentioned disadvantages or drawbacks. In addition, it is further desired to produce this gluconic acid and hydrogen peroxide solution with minimal space, using portable, modular, and small-scale components.

BRIEF SUMMARY

In one aspect of the disclosure described herein, a hydrogen peroxide and gluconic acid (HGA) production method, system, process, and composition is disclosed. In particular, the HGA method can include receiving an aqueous solution, wherein the aqueous solution is comprised of an organic material, water, and an enzyme. Here, the organic material can be glucose and the enzyme can be glucose oxidase. The method can further include receiving the aqueous solution at a vertical bubble column reaction chamber, wherein the reaction chamber comprises an enzymatic reaction between a gas phase and a liquid phase of the aqueous solution, thereby yielding a first solution comprising hydrogen peroxide, gluconic acid, and the glucose oxidase. The method can further include receiving the first solution at a separation chamber, wherein the separation chamber is comprised of a semi-permeable membrane having a pre-defined molecular weight barrier. Further, the method can include circulating the first solution through the separation chamber, wherein the circulating yields a second solution, and wherein the second solution is comprised of the hydrogen peroxide and gluconic acid but without glucose oxidase or no more than 100 ppm of glucose oxidase. Here, the second solution can be comprised of at least 0.1% wt. hydrogen peroxide and at least 0.1% wt. gluconic acid.

In another aspect of the disclosure described herein, a hydrogen peroxide and gluconic acid production method is disclosed that includes receiving an aqueous solution, wherein the aqueous solution is comprised of an organic material, water, and an enzyme, and receiving the aqueous solution at a reaction chamber, wherein the reaction chamber includes an enzymatic reaction between a vapor phase and a liquid phase, and wherein the enzymatic reaction results in a first solution includes hydrogen peroxide, gluconic acid, and the enzyme. The method further includes receiving the first solution at a separation chamber, wherein the separation chamber includes a semi-permeable membrane having a pre-defined molecular weight barrier. In addition, the method includes circulating the first solution through the separation chamber, wherein the circulating results in a second solution, and wherein the second solution includes the hydrogen peroxide and gluconic acid. In addition, the reaction chamber can be a vertical air bubble column. Further, the organic material can be glucose or dextrose syrup. Also, the enzyme can be glucose oxidase, the glucose oxidase can be free or immobilized within the reaction chamber. In addition, the semi-permeable membrane can be a vertical shell-and-tube configuration. Further, the pre-defined molecular weight barrier of the semi-permeable membrane can be at least 1,000 Daltons. Here, the semi-permeable membrane can block the enzyme from permeating there-through. In addition, the method can include receiving air bubbles from the reaction chamber at a defoamer or anti-foaming agent component, wherein the defoamer further includes a vapor-liquid separator.

The method can also include receiving the separated liquid from the vapor-liquid separator at the reaction chamber. Here, the second solution can have at least 0.1% wt. hydrogen peroxide and at least 0.1% wt. gluconic acid. In addition, the aqueous solution or the second solution can further include one or more additives or stabilizers comprised of one or more of: gluconic acid, sodium gluconate, urea, sodium stannate, and silver nitrate. The method can further include at least partially converting the gluconic acid into gluconate salts. N addition, the method can include converting the second solution into a third solution, wherein the third solution can include solid gluconic acid or solid gluconate salts. The method can also include converting the third solution into a fourth solution, wherein the fourth solution can include a mixture of gaseous hydrogen peroxide and water. Here, the method may also include separating the fourth solution into a fifth solution and sixth solution via a distillation column, wherein the fifth solution is comprised of hydrogen peroxide and water at a bottom region of the distillation column and the sixth solution is comprised of pure water from a top region of the distillation column.

In another aspect of the disclosure described herein, a hydrogen peroxide and gluconic acid production method is disclosed that includes receiving an aqueous solution, wherein the aqueous solution is comprised of glucose, purified water, and glucose oxidase enzyme, receiving the aqueous solution at a vertical bubble column reaction chamber. The method can further include delivering gas at a pre-defined pressure into the vertical bubble column reaction chamber, wherein the reaction chamber includes an enzymatic reaction that further includes a gas phase and a liquid phase, and wherein the enzymatic reaction results in a first solution having hydrogen peroxide, gluconic acid, and glucose oxidase. The method can further include receiving the first solution at a membrane separation chamber, wherein the separation chamber includes a semi-permeable membrane having a pre-defined molecular weight barrier, and circulating the first solution through the separation chamber, wherein the circulating results in a second solution, and wherein the second solution includes the hydrogen peroxide and gluconic acid. The method can also include receiving residual air bubbles from the reaction chamber at an air and liquid separation chamber, and separating the air and liquid from the residual air bubbles, and diverting the separated liquid into the reaction chamber.

In another aspect of the disclosure described herein, a hydrogen peroxide and gluconic acid production system is disclosed, wherein the system includes one or more storage tanks for storing an aqueous solution, wherein the aqueous solution is comprised of glucose-based composition, water, and glucose oxidase, and a vertical bubble reaction chamber for receiving the aqueous solution and initiating an enzymatic reaction between the aqueous solution and gas particles, thereby resulting in a first composition. The system can also include a separation chamber for receiving and circulating the first composition therein, thereby resulting in a second composition, wherein the second composition includes no more than 100 ppm of glucose oxidase, and a collection chamber for receiving and collecting the second composition from the separation chamber.

The above summary is not intended to describe each and every disclosed embodiment or every implementation of the disclosure. The Detailed Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following Detailed Description of various embodiments in connection with the accompanying drawings, in which:

FIG. 3A illustrates a partial cross-sectional side view of a separation chamber for the HGA production method and system of the disclosure described herein.

FIG. 3B illustrates a partial cross-sectional top view of the separation chamber of FIG. 3A.

FIG. 3C illustrates a partial cross-sectional side view of a semi-permeable membrane of the separation chamber of FIG. 3A.

DETAILED DESCRIPTION

In the Brief Summary of the present disclosure above and in the Detailed Description of the disclosure described herein, and the claims below, and in the accompanying drawings, reference is made to particular features (including method steps) of the disclosure described herein. It is to be understood that the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment.

Figure 1:
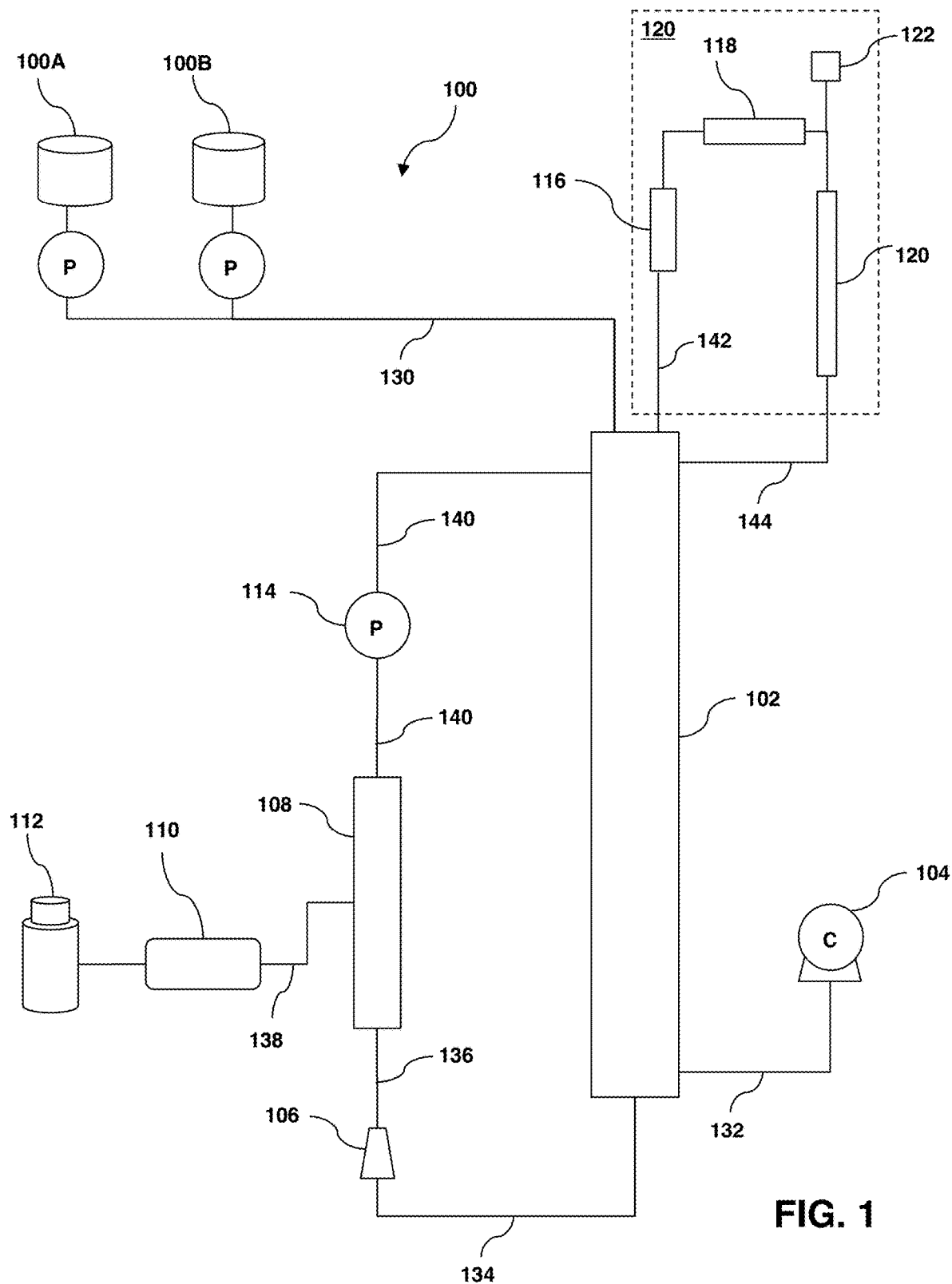
FIG. 1 illustrates an overview schematic diagram for one non-limiting embodiment of a hydrogen peroxide and gluconic acid (HGA) production method and system of the disclosure described herein.

FIG. 1 illustrates one non-limiting embodiment of a schematic diagram for a plant, system, and method/process 100 for producing a hydrogen peroxide and gluconic acid (HGA) composition. Here, plant, system, and process 100 may be comprised of a large-scale industrial system requiring anywhere from 1,000 to 1,000,000 square foot of space for its components, or a small-scale system requiring anywhere from 1 square feet to 999 square feet of space. In addition, each component 100A up to and including 144, and sub-components, of process 100 may also be modular in design. For example, such a modular system may include but is not limited to: functional partitioning into discrete scalable, reusable modules consisting of isolated, self-contained functional elements or components; use of well-defined modular interfaces, including object-oriented descriptions of module functionality; or ease of change or modification to integrate industry standards for certain interfaces. In addition, such a modular system for process 100 can provide a reduction in cost, reduced learning time, and increased flexibility and customization for customers.

Still referring to FIG. 1, process 100 can generally include a water source 100A and a glucose or dextrose source 100B. In particular, source 100A can include distilled water ($H_2O$), purified water, oxygenated water, super oxygenated water, or any water having additives. For example, such additives may include: electrolytes, anti-microbial agents, vitamins such as vitamin C, vitamin D, vitamin A, B-complex; as well as minerals, such as calcium, strontium, fluorine, potassium, and sodium; and chemicals for aromatherapy, appetite suppressants, herbal mixtures, protein additives, antibiotics, nicotine, antioxidants, *ginseng*, caffeine, or other stimulants, and medicines. Glucose source 100B may include any type of organic or inorganic glucose ($C_6H_{12}O_6$), α-glucopyranose, β-glucopyranose, β-glucopyranose, dextrose, polysaccharides such as starch and glycogen, or monosaccharides such as sucrose and lactose, sugar, maltodextrin, or high fructose corn syrup, among others. In addition, glucose source 100B may further include various additives, such as one or more stabilizers, enzymes, or co-enzymes. For example, such stabilizers, enzymes, or co-enzymes may prevent retrogradation of the nutritional product for a period of at least 12 hours, including at least 24 hours, including at least 48 hours, including at least 7 days, including at least 1 month, including at least 2 months, including at least 4 months, including at least 6 months, and including at least 9 months, 12 months, 18 months, or longer.

In addition, either of source 100A and 100B, or any additional source, can include the catalyst enzyme glucose oxidase. Glucose oxidase may also be referred to herein as glucose oxyhydrase, beta-D-glucose oxidase, or oxygen 1-oxidoreductase. However, it is contemplated within the scope of the disclosure described herein that any other type of enzyme may also be used in combination with or in lieu of glucose oxidase, including but not limited to pyranose oxidase, or glucose 2-oxidase, engineered or synthetic glucose oxidase, oxalate oxidase, fructose oxidase, oxygenate oxidase, or pyranose: oxygen 2-oxidoreductase. However, the preferred enzyme for this HGA production of the disclosure is glucose oxidase.

In other embodiments, source 100A and 100B may also be comprised of one single source, wherein the water and glucose (dextrose syrup) composition are pre-mixed or pre-agitated as a slurry in a container or drum to a desired concentration such as a weight % ratio of 97%:3%, 95%:5%, or 90%:10%, or 85%:15% of water to glucose concentrations. Such mixing and agitating may include mechanical mixing or agitation via heat treatment at a desired temperature.

Still referring to FIG. 1, in the current embodiment, water source 100A may include a greater than 99% purified distilled water of approximately 100 gallons and glucose source 100B may include approximately 55 gallons of 70% wt. organic dextrose corn syrup composition. Alternatively, water source 100A can be purified on-demand from a local tap source using continuous reverse osmosis and deionization systems. As such, references to 100A, 100B, liquid/working solution 200 throughout the disclosure also refer to the contents of the sources, namely, water, glucose, glucose oxidase, and any other stabilizer, element, or additive disclosed above.

Still referring to FIG. 1, in one method of operation each source 100A (water) and 100B (glucose) may include one or more pumps for pumping the water 100A and glucose 100B from the outlets of the sources into piping or line 130, such as via a tee fitting, wye fitting, or another similar component. For example, the pump for water source 100A may include a 400 GPD booster pump and the pump for glucose source 100B may include a dextrose diaphragm dosing pump. However, it is contemplated within the scope of the disclosure that any type of pump may be used for the HGA production system and process, including but not limited to: centrifugal pumps, positive displacement or reciprocating pumps, impulse pumps, velocity pumps, gravity pumps, steam pumps, or valve-less pumps, among others. Further, each line from source 100A and 100B may include one or more control valves, check vales, flow meters, and pressure gauges for monitoring the input and output of each pump and/or source. Here, the mixture of water 100A and glucose 100B, or collectively liquid/working solution 200, may flow at a rate of approximately 500 mL/min, or a range from 200 mL/min to 12 L/min within line 130, wherein line 130 is connected to the inlet of reaction chamber 102 and in fluid communication therewith. In addition, line 130 may also have a steady pressure of approximately 60 psig, or anywhere from 1 psig to 1,000 psig. Here, it is contemplated within the scope of the disclosure described herein that line 130 may also include additional components, such as a mixing, purifying, or agitating components for the contents of source 100A and 100B. Further, it is contemplated within the scope of the disclosure that in lieu of line 130, each source 100A and 100B may include their own independent line wherein each independent line is connected to inlets at reaction chamber 102.

Still referring to FIG. 1, reaction chamber 102 may be comprised of a pressure vessel or container having an air column or bubble column configuration, which will be described in more detail later in the disclosure with respect to FIG. 2. Further, reaction chamber 102 may also include one or more sources of compressed air to be introduced via one or more nozzles/orifices within chamber 102 in order to sparge the air from a gas phase into a liquid phase within reactor 102. In particular, the air or gas compressor 104 may compress air or a gaseous composition and direct the air via line 132 into a gas/air filter element and subsequently into the inlet of reaction chamber 102. In addition, reaction chamber 102 may include a separate inlet or charging port for introducing an enzyme such as a free or immobilized glucose oxidase into chamber 102 to facilitate the enzymatic reaction. Here, a first yielded product solution as a result of the reaction within chamber 102, namely, gluconic acid, hydrogen peroxide, and free glucose oxidase enzymes, can be pumped or directed to line 134 which is further directed into a pressure reducer or regular 106, wherein regulator 106 can reduce the incoming pressure, such as from 60 psig to 25 psig. From regulator 106, the first product working solution may then be pumped or directed to a separation chamber 108, wherein separation chamber 108 will be described in more detail later in this disclosure with respect to FIG. 3.

Still referring to FIG. 1, separation chamber 108 includes one or more membrane or filtering component that separates the glucose oxidase enzyme from the first product working solution, thereby resulting in a final second product solution having at least 0.1% wt. hydrogen peroxide and at least 0.1% wt. gluconic acid. In addition, the final product solution may also include minimal or trace amounts of other additives, such as one or more stabilizers, which may have been introduced at the beginning of the process or after separation chamber 108. In addition, the final product solution may be pumped or directed out of chamber 108 via line 138 and into an optional testing chamber 110. Here, testing chamber 110 may test, verify, or adjust the concentrations and/or purity of the final product solution. After optional testing chamber 110, the final product solution may be collected at container or storage tank 112 or packaged for use. Here, in one embodiment, tank 112 may receive the final product solution at a rate of 300 mL/min with a concentration of 1% wt. hydrogen peroxide and 6% wt. gluconic acid, and less than 500 ppm glucose.

Still referring to FIG. 1, prior to collecting the final product solution, the first product working solution is continuously recirculated in the process 100 loop via one or more pumps, such as peristatic pump 114, through lines 140, reaction chamber 102, line 134, regulator 106, and reaction chamber 108 until a desired final product solution, concentration, and purity of combined hydrogen peroxide and gluconic acid is achieved. For example, in one embodiment, if there is a separation chamber 108 with a membrane, then process 100 can recirculate the final product working solution, so that the membrane can operate in a tangential flow filtration mode to prevent it from deteriorating, rapidly fouling, or lose its efficacy. In another embodiment that does not include a separation chamber 108 or a membrane, then the working solution does not need to be recirculated within process 100.

Figure 10:
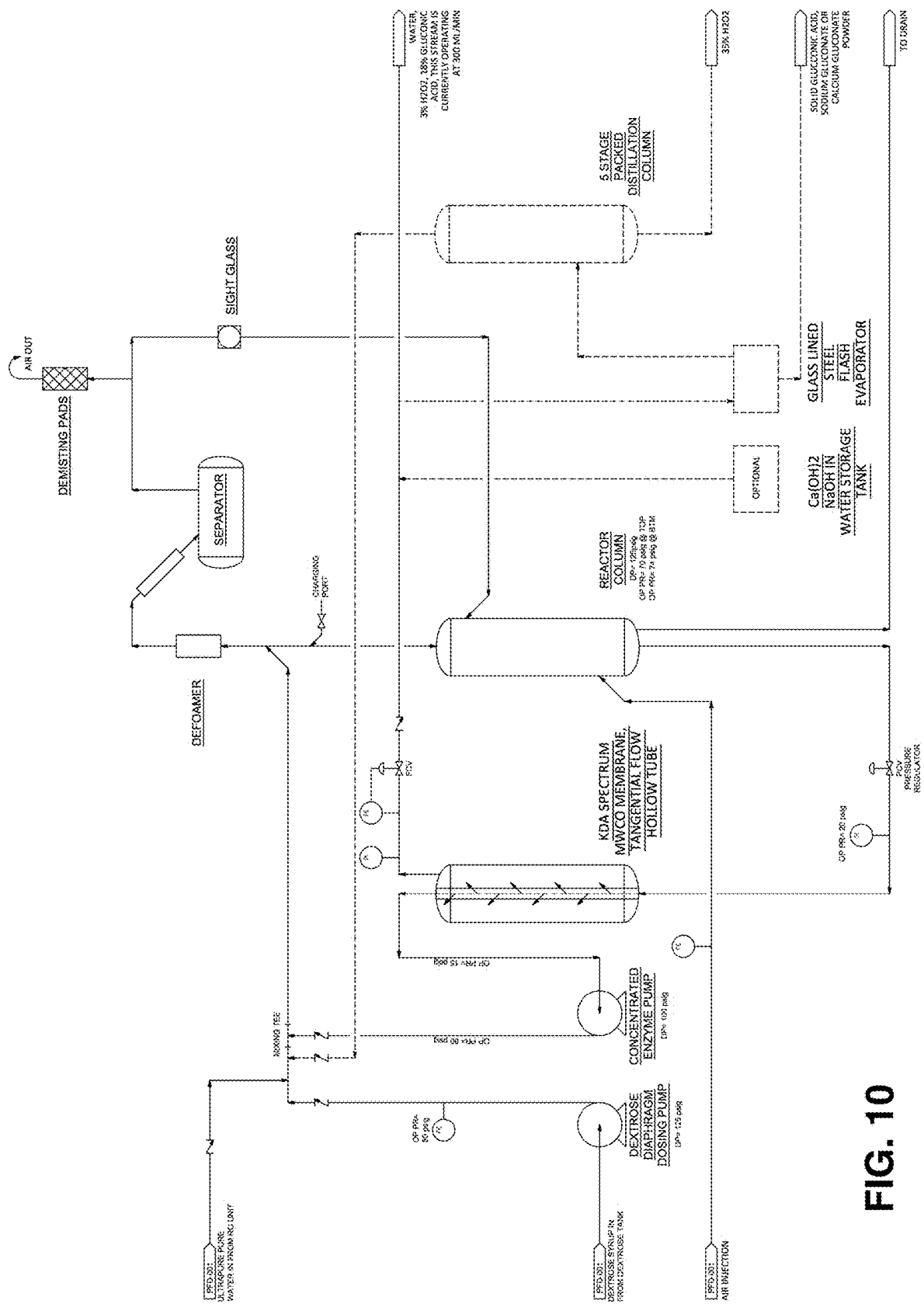
FIG. 10 illustrates an overview schematic diagram for another non-limiting embodiment of the HGA production method and system of the disclosure described herein.

Still referring to FIG. 1, process 100 may also include optional recycling or defoaming loop 130 for controlling or minimizing excess air bubbles or foam production within reaction chamber 102. Specifically, line 142 may draw and direct residual foam or air bubbles from chamber 102 into a defoamer component 116, wherein defoamer 116 may include one or more defoaming or anti-foaming agents for minimizing or reducing air or gas bubbles. From defoamer 116, the first defoamed solution can further be directed into a liquid-vapor separator 118, wherein the air/vapor is separated from the liquid. From separator 118, the vapor is directed to a demisting pad component 122 and further directed out to the atmosphere, and the separated liquid solution is directed to a sight-glass component 120 or any type of gauge or float switch for measuring the amount of liquid in the line. Here, the separated liquid may include the original contents of source 100A and 100B, or namely, a combination of hydrogen peroxide, glucose, water, glucose oxidase enzyme, and stabilizers. As such, the separated liquid solution is re-introduced and re-directed back to reaction chamber 102, thereby improving its efficiency and final yield. Here, FIG. 10 illustrate another more detailed embodiment for the HGA production process of the disclosure described herein, which will be addressed later in this disclosure.

Figure 2:
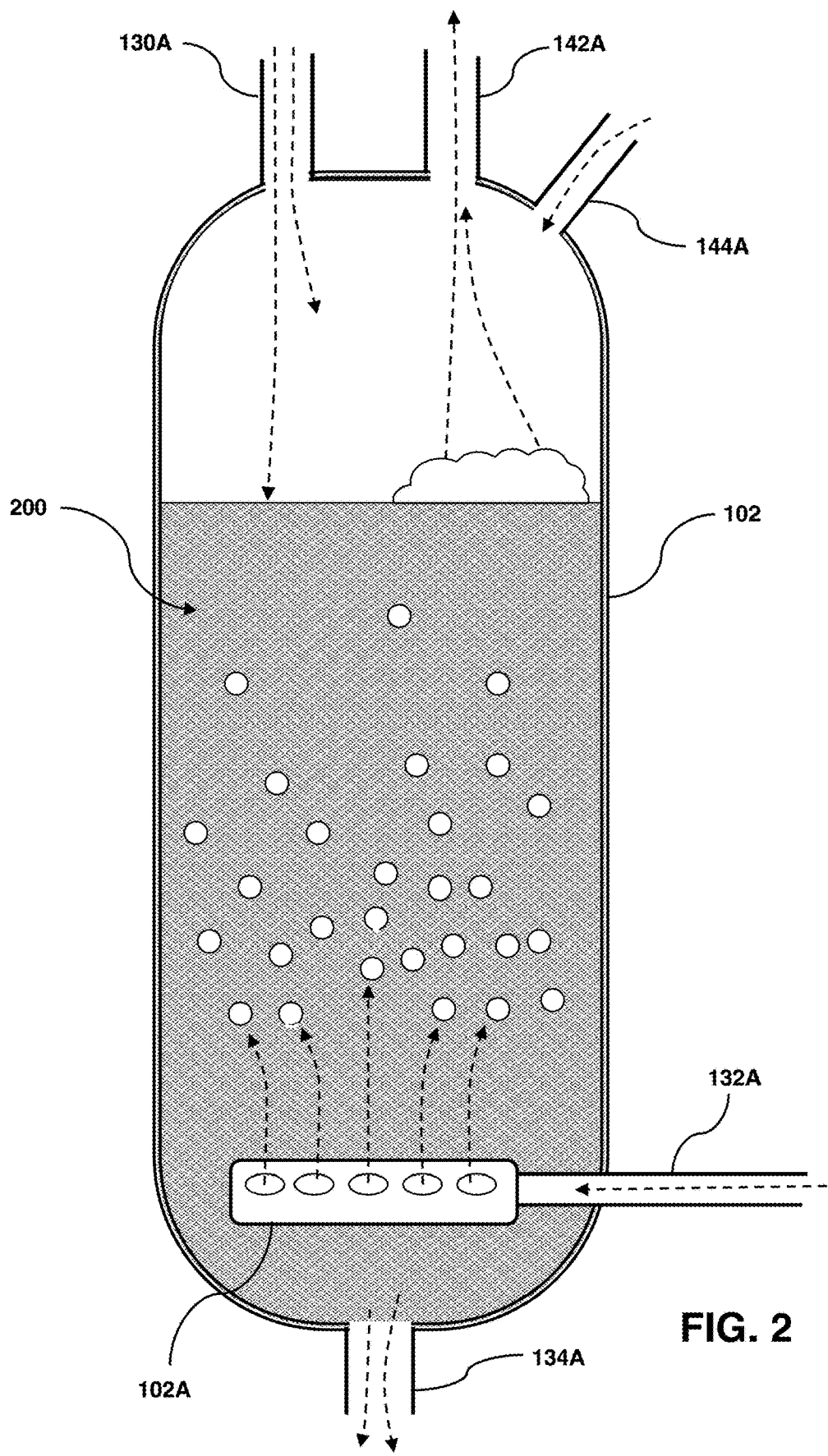
FIG. 2 illustrates a partial cross-sectional view of a reaction chamber for the HGA production method and system of the disclosure described herein.

FIG. 2 illustrates a partial cross-sectional view for one non-limiting embodiment of the bubble column reaction chamber 102 of the disclosure described herein, for illustrative purposes only. Here, chamber 102 can include port or inlet 130A which connects to line 130, port or outlet 142A which connects to line 142, port or inlet 144A which connects to line 144, port or inlet 132A which connects to line 132, and port or outlet 134A which connects to line 134. In operation, chamber 102 receives working aqueous solution 200 via line 130 from sources 100A and 100B, which may include a combination of water, glucose, hydrogen peroxide, glucose oxidase enzyme, and one or more stabilizers, among others. At around the same time, prior to, or simultaneously, reaction chamber 102 may receive compressed air or gas having an approximate pressure of 90 psig via line 132 into inlet 132A and dispersed via a nozzle or sparger 102A. In particular, sparger 102A may be comprised of a nozzle, orifice plate, sponge, or a sintered plate that allows gas or air to be vertically injected upward from sparger 102A and to be mixed with the liquid phase of working solution 200 inside the bubble column or reaction chamber 102. In addition, to avoid large air bubbles, sparger 102A may be configured such that air bubbles are limited to a certain size, such as 70 microns or less, depending on the filter element size, air velocity, and viscosity of liquid working solution 200, in order to improve mass transfer rates between the vapor phase and the liquid phase within chamber 102. Specifically, the introduction of a high volume of oxygen ($O_2$) into the reactor improves the presence of glucose oxidase in the solution during hydrogen peroxide production, since hydrogen peroxide is known to reduce or break down glucose oxidase. In other words, an excess of oxygen into the reaction chamber counters, eliminates, or at minimum reduces the potential deleterious effect of hydrogen peroxide on glucose oxidase.

Still referring to FIG. 2, the reaction time within chamber 102 can be for approximately 60 minutes, but may range anywhere from 5 seconds up to and including 360 days, depending on volume and flow rates. In one embodiment, gas compressor 104 is configured to deliver oxygen for a period of approximately 60 minutes in a continuous mode operation. However, compressor 104 may also be configured to deliver oxygen intermittently or based on a pre-defined schedule or period. Here, the volume of chamber 102 is approximately 19.75 liters, or may range anywhere from 1 ounce up to and including 500,000 liters, or any other suitable capacity. In addition, process 100 may be configured such that there are two or more reaction chambers 102 operating in series or in parallel with respect to each other, which will be described later in the disclosure with respect to FIGS. 5 and 6.

FIGS. 3A-3C illustrate various views for one non-limiting embodiment of the separation chamber of the disclosure described, for illustrative purposes only. Here, separation chamber 108 can include a tubular housing 202 that further houses many tubular dialysis membranes in parallel 204. In addition, housing 202 further includes end caps 220 and 220, for receiving and outputting the aqueous working solution 200. In particular, end cap 220 includes an inlet port 210 which connects to line 136 for receiving the circulating liquid solution 200. In addition, chamber 108 may also include an optional inlet port 212 for introducing other additives into the liquid solution. Here, the received liquid solution at inlet 210 may be pumped, injected, or circulated within the interior space 206 of tubular membrane 204. Here, membrane 204 can either be suspended or freely floating within housing 202, or in the alternative, membrane 204 can be coupled or fixed to housing 202 of chamber 108.

Still referring to FIGS. 3A-3C, membrane 204 can have a specified or pre-determined molecular weight barrier cut-off. More specifically, any substance, enzyme, compound, solution, carrier, or molecules within the interior chamber space 206 of membrane 204 that are larger in molecular weight than the specified or pre-determined cut-off will be trapped within the retentate space 206 of membrane 204. In contrast, any substance, compound, solution, or molecules that are less than the pre-determined cut-off will diffuse or permeate through the membrane. In the current embodiment, membrane 204 is made of a semi-permeable material that can have a pre-defined 1,000, 3,000, 5,000 or 10,000 Dalton molecular weight barrier cut-off or threshold, however, it is contemplated within the scope of the invention that any suitable molecular weight barrier cut-off may also be used, including but not limited to 100 Daltons up to and including 150,000 Daltons. Here, the aqueous working solution 200 may have elements or enzymes, such as glucose oxidase, that have a molecular weight that is larger than the specified cut-off for the membrane. For example, as shown in FIG. 2C, the oxidase glucose enzyme of working solution 200 can be trapped in the retentive side of the membrane 204 and not allowed to permeate through, whereas the produced hydrogen peroxide and gluconic acid (or any other additive with a size less than the pre-defined cut-off) can permeate through as the final product solution to be collected. Accordingly, the resulting final product solution 200 can be pumped or diverted out of housing 202 of chamber 108 through outlet 214 and to one or more testing chambers, collection chambers, or for additional processing and circulation.

Still referring to FIGS. 3A-3C, outlet 214 may also be connected to line 140 to allow for the continuous flow of the working solution 200 within the closed loop cycle of process 100. For example, in one embodiment, working solution 200 may be dispersed or allowed to flow through separation chamber 108 for a period of approximately 5 minutes prior to the final product solution being collected. Specifically, it is contemplated within the scope of the disclosure described herein that through each re-circulation or iteration of working solution 200 through reaction chamber 102 and separation chamber 108, the hydrogen peroxide and gluconic acid concentration of the liquid working solution 200 increases, provides a higher yield or % wt. of either hydrogen peroxide or gluconic acid, such as in a batch mode operation. For example, in one embodiment, length of time and/or flow rate of the working solution circulating within process 100 may be the only variable(s) that control the concentrations or % wt. of each the hydrogen peroxide and gluconic acid within the final product composition. Here, batch mode operation is generally wherein there are no liquid streams flowing into or out of the reactor. In this mode, the concentration will increase with time as long as glucose and oxygen are still present. However, in another embodiment, such as in a continuous mode operation, a steady state condition would be reached wherein the concentration of the working solution 200 leaving the separation chamber 108 would remain substantially constant with respect to time.

Figure 4:
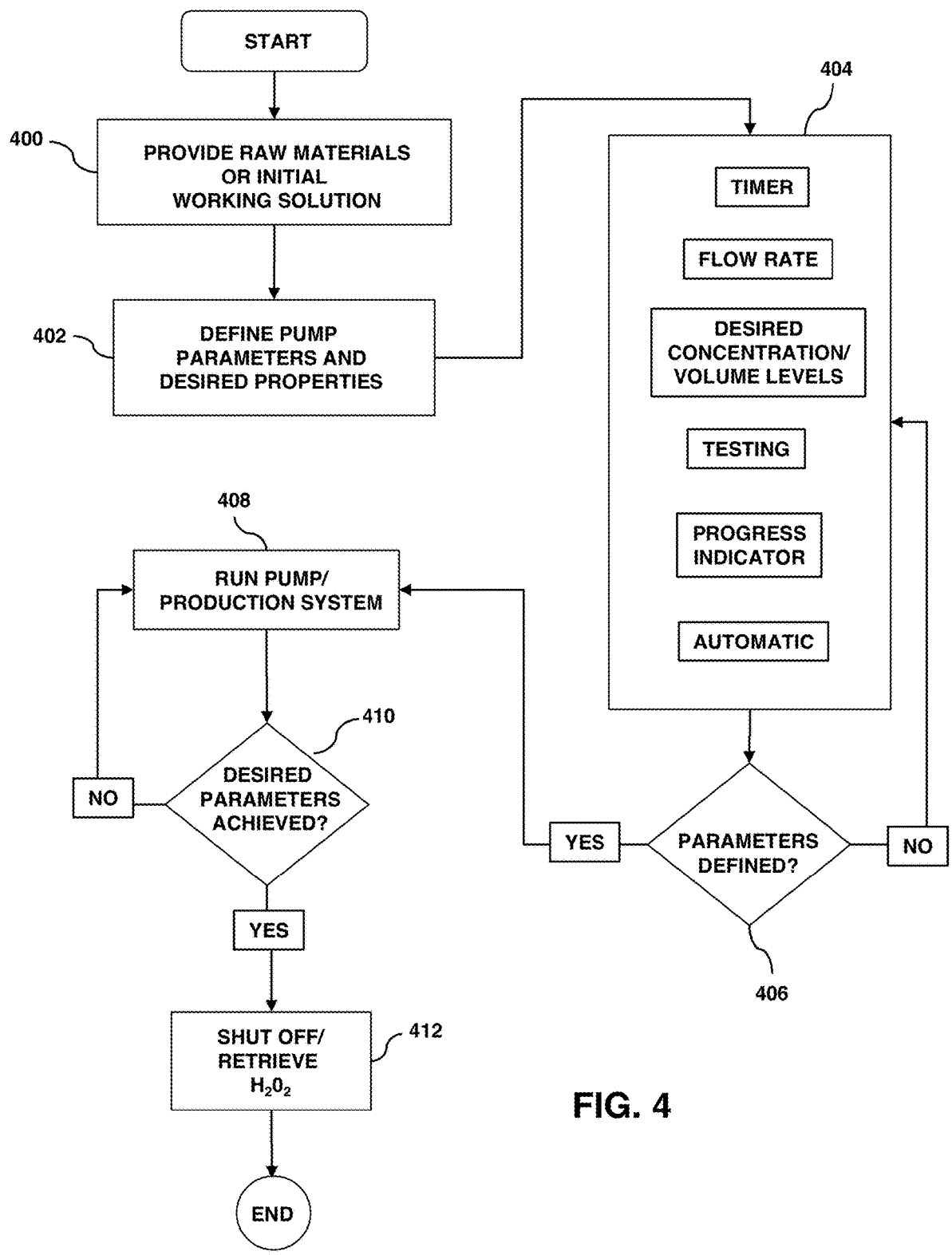
FIG. 4 illustrates a block diagram of a process flow for one non-limiting embodiment of an automated, continuous method of HGA production of the disclosure described herein.

FIG. 4 illustrates one non-limiting for a method of automating the HGA production system. Specifically, the process can start at step 400, wherein raw source materials or initial working solution are introduced into the production system, namely, the reaction bubble chamber 102. At step 402, one or more pumps within the system may be programmed or receive operational parameters for running one or more production pumping cycles. Here, it is contemplated within the scope of the disclosure described herein that the pump may include one or more control units, controllers, microprocessors, memory, and storage units for executing one or more pre-programmed or user-defined operations, applications, logic, algorithms, software, and commands. More specifically, at step 404, a user may define or schedule a timed operation within a timer or scheduling module of the pump, such as start/stop times, day/month/year, daily, monthly, yearly, single-use, or periodic operations. In addition, the user may also define or set a constant or variable flow-rate for the pump operation. Further, user may also define or set a desired threshold hydrogen peroxide concentration or volume levels. More specifically, in such an embodiment, the pump may continue to operate and re-circulate the working solution within the system until a pre-defined or user-defined hydrogen peroxide concentration and gluconic acid level is reached, and wherein the pump may shut-off automatically, or in the alternative, notify or alert one or more users.

Still referring to FIG. 4, the aforementioned pump may also include a testing module for automatically, periodically, or continuously testing the hydrogen peroxide concentration levels of the working solution passing through the pump. Further, the pump may also include a progress indicator for indicating various factors, including but not limited to: current concentration levels, desired concentration levels, flow rate, estimated time remaining until completion of one or more production cycles, temperatures, environmental conditions, stable or un-stable conditions, and any notifications, alerts, or errors, among others. Also, the pump may include functionality for automatic, semi-automatic, or manual operation.

Still referring to FIG. 4, at step 406, once the parameters have been defined, the process can proceed to step 408. At step 408, the process can commence the hydrogen production and gluconic acid cycle. It is contemplated within the scope of the disclosure that each cycle can operate continuously in operation from one (1) minute up to and including 365 days, depending on the intended application, use, volume, and desired hydrogen peroxide and gluconic acid concentration levels. At step 410, once the one or more pre-defined or threshold parameters are reached, the process may then proceed to step 412, wherein the pump and production system may automatically shut-off, rest, or repeat the cycle after a pre-determined time. In addition, at this step, the working solution batch having the hydrogen peroxide composition may be extracted, removed, dispensed, or packaged for distribution. Alternatively, the working solution batch may be re-introduced back into the production system in full or in part for additional hydrogen peroxide and gluconic acid production.

Figure 5:
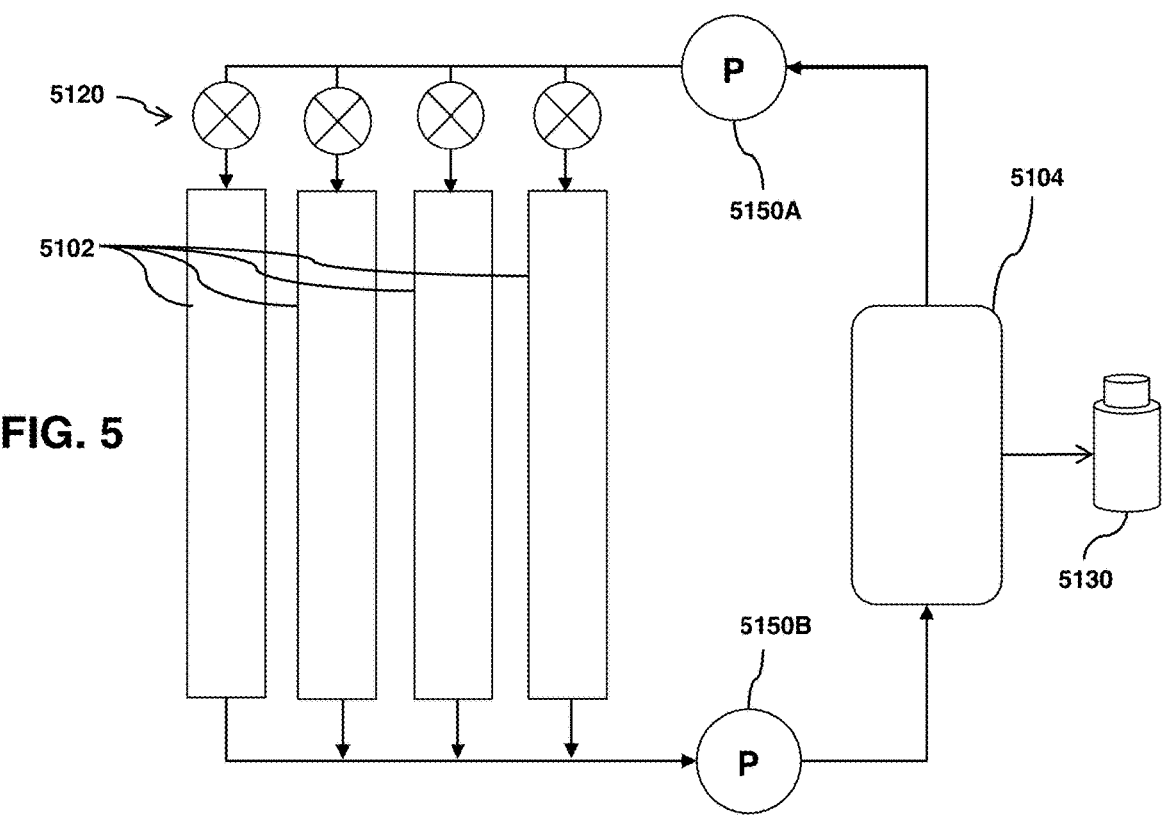
FIG. 5 illustrates an overview schematic diagram for another non-limiting embodiment of the HGA production method and system of the disclosure described herein.

FIG. 5 illustrates another non-limiting embodiment for an HGA production system and process of the disclosure described herein. In this embodiment, the system may include a plurality of bubble column reaction chambers 5102 connected in parallel and a plurality of valves 5120 controlling the inlet of each chamber. One or more of the reaction chambers 5102 may be operational at any given time depending on the intended use, application, volume, and hydrogen peroxide concentration desired. The system may also include a first pump 5150A and second pump 5150B in order to further provide additional flow rate and assure constant pump head pressure throughout the process for efficiently circulating the working solution. In addition, the system includes at least one membrane separation chamber 5104, wherein the resulting hydrogen peroxide and gluconic acid batch 5130 may be collected and stored. It is contemplated within the scope of the disclosure that any one or more valves or thermodynamic components may also be incorporated into the system of FIG. 5.

Figure 6:
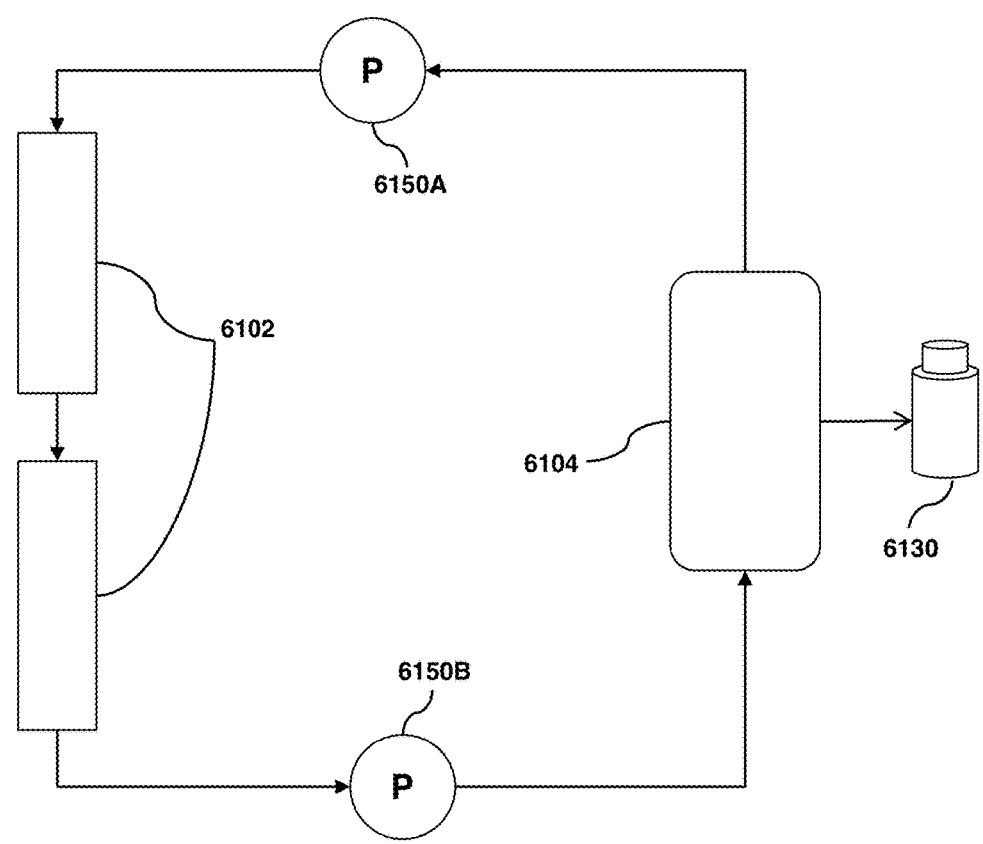
FIG. 6 illustrates an overview schematic diagram for another non-limiting embodiment of the HGA production method and system of the disclosure described herein.

FIG. 6 illustrates another embodiment for a hydrogen peroxide and gluconic acid production system of the disclosure described herein. In this embodiment, the system may include a plurality of bubble column reaction chambers 6102 connected in a series configuration wherein a plurality of pumps 6150A and 6150B further circulate the working solution through at least one separation chamber 6104, wherein the working solution containing hydrogen peroxide and gluconic acid batch 6130 may be collected and stored. Here, it is contemplated within the scope of the disclosure described herein that the addition of production chambers connected in series can further help improve the efficiency of the reaction and provide a higher yield or higher quantities. Also, the addition of more than one separation chamber can further help purify the working solution and separate the glucose oxidase, or any other un-desired additive, from the final hydrogen peroxide and gluconic acid solution. It is contemplated within the scope of the disclosure that any one or more valves or thermodynamic components may also be incorporated into the system of FIG. 6.

Figure 7:
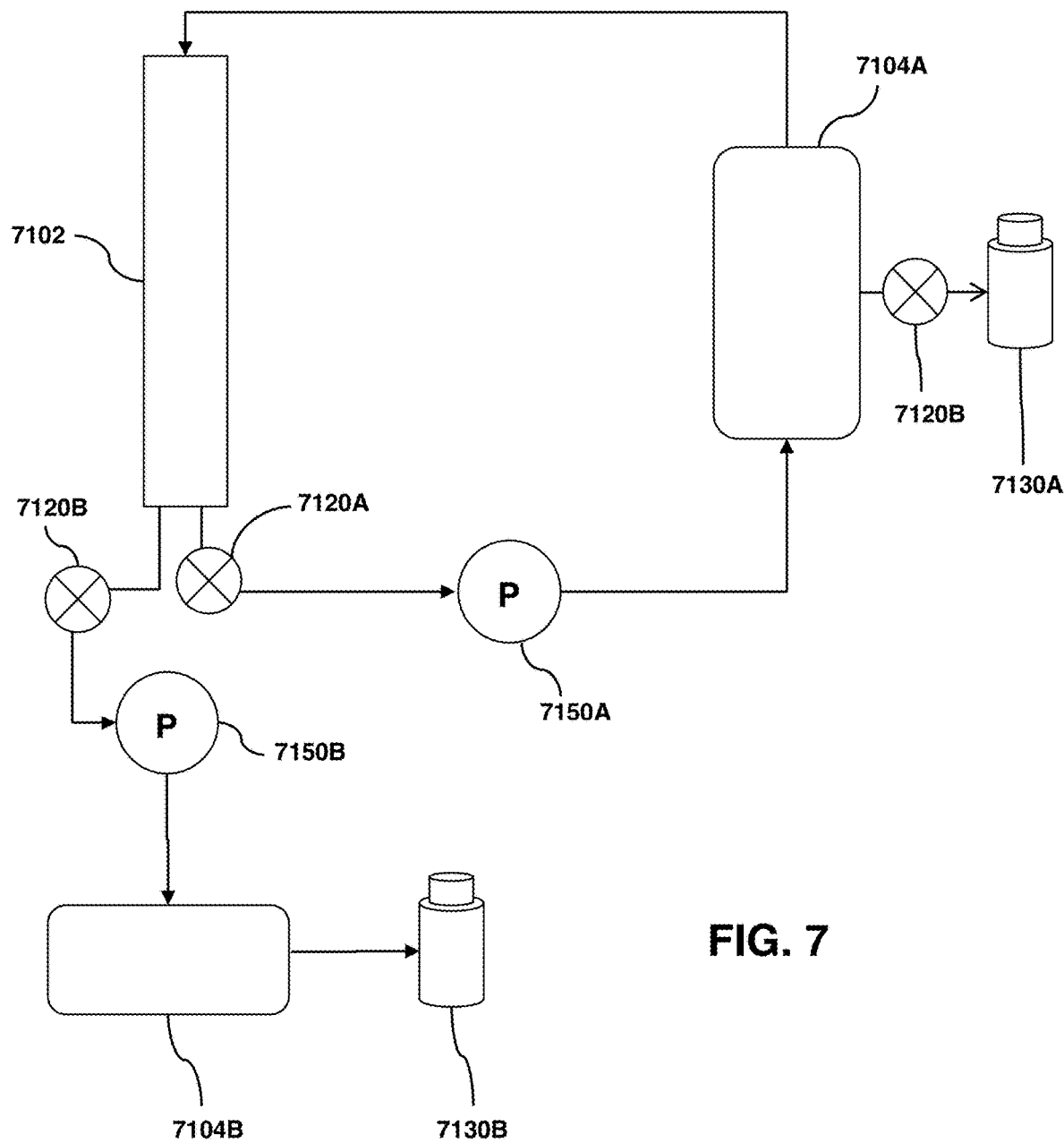
FIG. 7 illustrates an overview schematic diagram for another non-limiting embodiment of the HGA production method and system of the disclosure described herein.

FIG. 7 illustrates another embodiment for a hydrogen peroxide and gluconic acid production system of the disclosure described herein. In this embodiment, the system may include a bubble column reaction 7102 in communication with a first membrane separation chamber 7104A and a second membrane separation chamber 7104B. In this embodiment, a pre-defined volume or percentage of the working solution may be diverted to separation chamber 7104B via opening of valve 7120B and operation of pump 7150B thereby directing the working solution to separation chamber 7104B to be later recovered or collected as batch 7130B. The remaining working solution within the system may continue to circulate through pump 7150A, separation chamber 7104A and back through reaction chamber 7102. It is contemplated within the scope of the disclosure that any one or more valves or thermodynamic components may also be incorporated into the system of FIG. 7.

Figure 8:
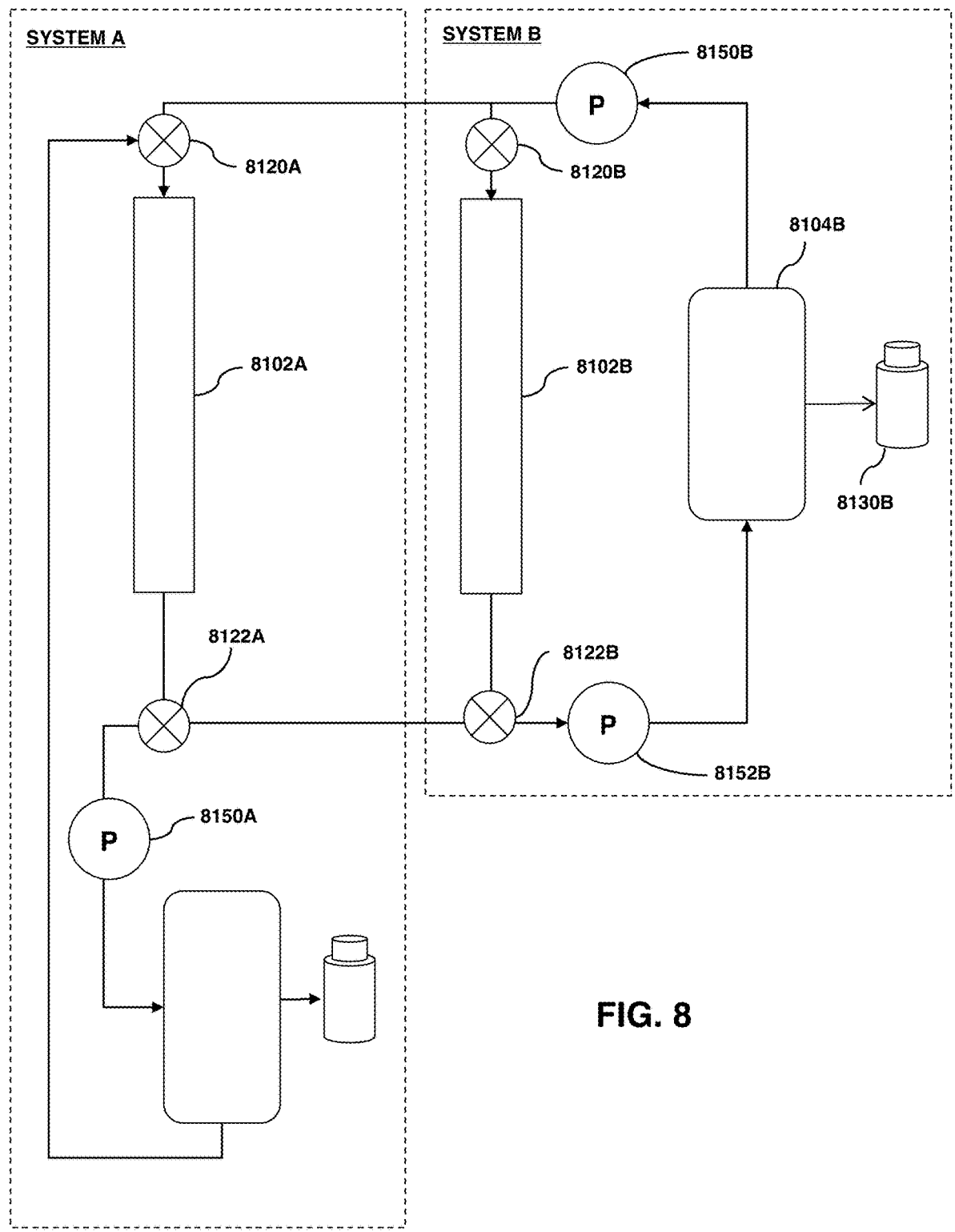
FIG. 8 illustrates an overview schematic diagram for another non-limiting embodiment of the HGA production method and system of the disclosure described herein.

FIG. 8 illustrates another embodiment for a hydrogen peroxide and gluconic acid production system of the disclosure described herein. In this embodiment, the system may be a two-part system that can work in unison with each other or independent of each other. Here, system A may include a bubble column reaction chamber 8102A that may be isolated from system B by closing three-way valves 8120A and 8122A. Such a two-part system may be used in a production scenario wherein two or more separate hydrogen peroxide and gluconic acid concentration levels or volumes may be desired. Similarly, system B may be isolated from system A via closing of three-way valves 8120B and 8122B. Each system can include its own independent pumping systems and collection chambers. Alternatively, both system A and system B can operate in unison to improve efficiency and provide a higher yield of both hydrogen peroxide and gluconic acid. It is contemplated within the scope of the invention that any one or more valves or thermodynamic components may also be incorporated into the system of FIG. 8.

Figure 9A:
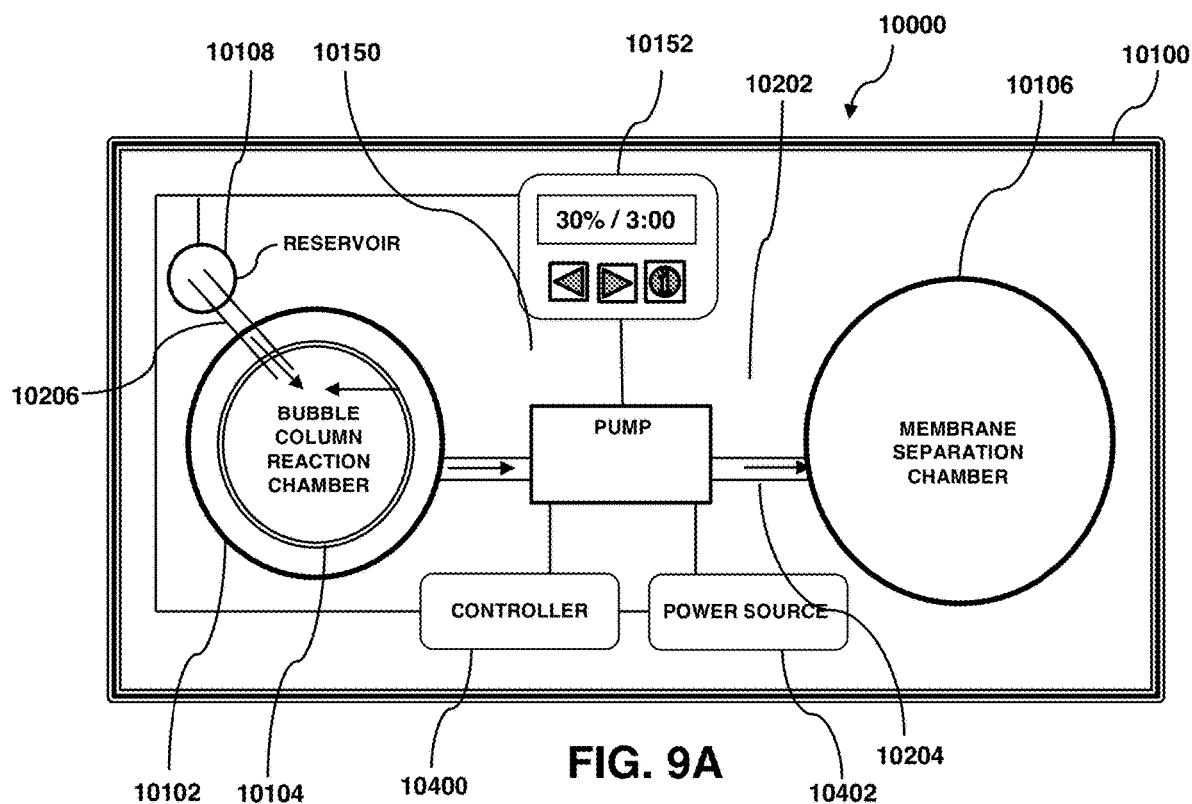
FIG. 9A illustrates a partial top view for one non-limiting embodiment of a portable, mobile, and modular apparatus for producing the HGA of the disclosure described herein.
Figure 9B:
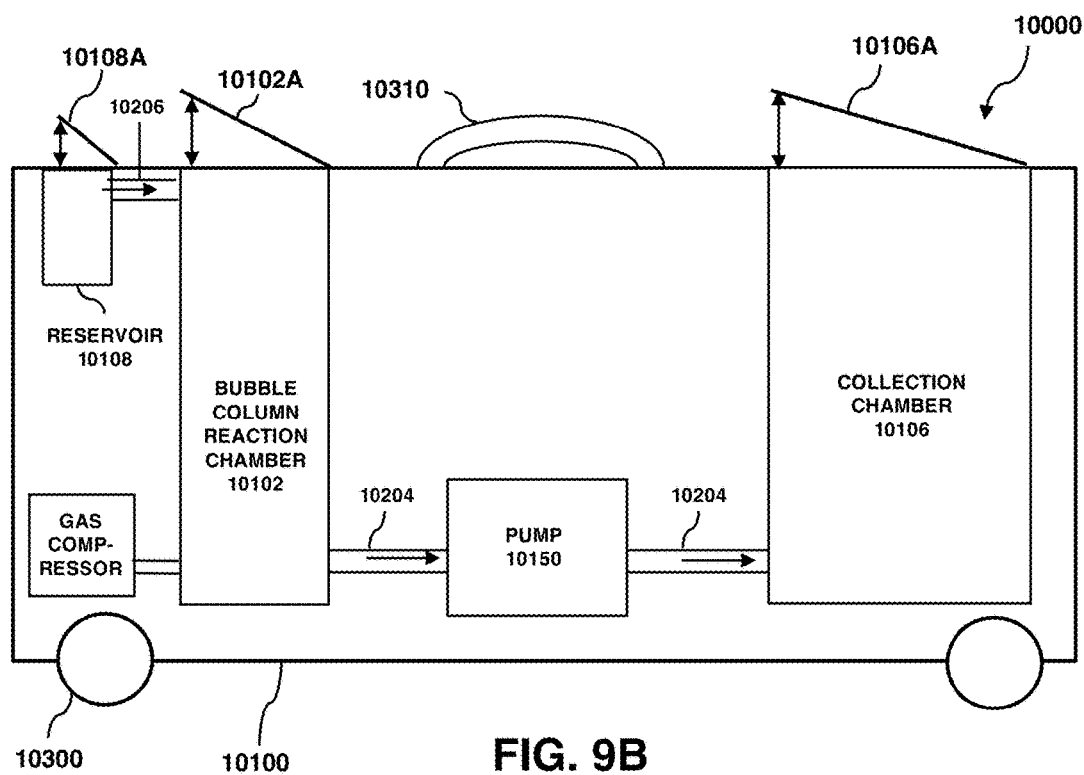
FIG. 9B illustrates a partial cross-sectional side view the portable, mobile, and modular apparatus of FIG. 9A.

FIGS. 9A-9B illustrate another embodiment for the hydrogen peroxide and gluconic acid production system and apparatus of the disclosure described herein configured as a single portable, mobile, and modular unit. FIG. 9A illustrates a top view of the portable unit 10000, wherein a top cover is removed, thereby illustrating some of the interior components. Specifically, unit 10000 can include a casing or housing 10100 for enclosing a production chamber 10102, semi-permeable membrane 10104 within the production chamber, collection chamber 10106, source working solution reservoir 10108, pump 10150, user interface 10152, tubes 10202, 10204, and 10206, controller or control unit 10400, and a power source 10402, among others. However, it is contemplated within the scope of the disclosure described herein that any other parts, components, or control devices may also be included in combination or in lieu of the aforementioned components.

Still referring to FIG. 9A, controller 10400 can include a microprocessor, memory, storage device, logic, software, application, algorithm, and programming stored thereon, among others, for controlling operation of the hydrogen peroxide production and gluconic acid method, system, and apparatus of the disclosure described herein. Here, logic, software, application, algorithm, and programming may include any non-transitory computer readable medium storing thereon a program, which when executed by a computer, causes the computer to perform a method or function. Further, controller 10400 can further electrically communicate and send/receive commands with pump 10150, graphical user interface 10152, reservoir 10108, reaction chamber 10102, and separation chamber 10108. Here, tube 10204 is in fluid communication with production chamber 10102 wherein its contents are outputted to pump 10150 and collection chamber 10106. Tube 10202 is in fluid communication with collection chamber 10106 wherein its contents are outputted to pump 10150 and production chamber 10102.

FIG. 9B illustrates a partial cross-sectional side view of the portable hydrogen peroxide production unit 10000, for illustrative purposes only. In particular, unit 10000 is further shown having a gas compressor on-board to provide sparging within reaction chamber 10102. In addition, the mobile unit can further include a plurality of wheels or casters 10300 and handle 10130 for portability and mobility. Further, housing 10100 can further include access and closure part 10106A for accessing, removing, or servicing chamber 10106, access and closure part 10102A for accessing, removing, or servicing chamber 10102, and access and closure part 10108A for accessing, filling, or emptying reservoir 10108. Here, it is contemplated within the scope of the disclosure herein that any of parts 10102A, 10106A, and 10108A may be any hinge operated, pivoting, locking, or sliding access lid, cover, closure, or seal. It is also contemplated within the scope of the disclosure described herein that unit 10000 may also be configured without a separation/membrane chamber.

FIG. 10 illustrates another embodiment for a hydrogen peroxide and gluconic acid production system of the disclosure described herein. Here, the HGA production process may also include an additional process for converting the final working solution having gluconic acid to metal gluconate, such as sodium, calcium, and zinc, among others. Specifically, this additional process can include mixing the hydrogen peroxide and gluconic acid solution with the corresponding metal hydroxide, thereby resulting in a rapid acid/base reaction which further results in a hydrogen peroxide and metal gluconate solution. The hydrogen peroxide and solvent water can be separated from the metal gluconate via vacuum flash evaporation. For instance, this process can be done at 0.1 atm and 140-150° F. This results in a solid, purified metal gluconate salt and a vapor of water and hydrogen peroxide. This vapor can be further purified by vacuum distillation to create concentrated hydrogen peroxide solutions. For instance, vacuum distilling a water and hydrogen peroxide solution at 0.1 atm and 135° F. allows concentrations of hydrogen peroxide to be achieved in excess of 30% wt. in water.

Figure 11:
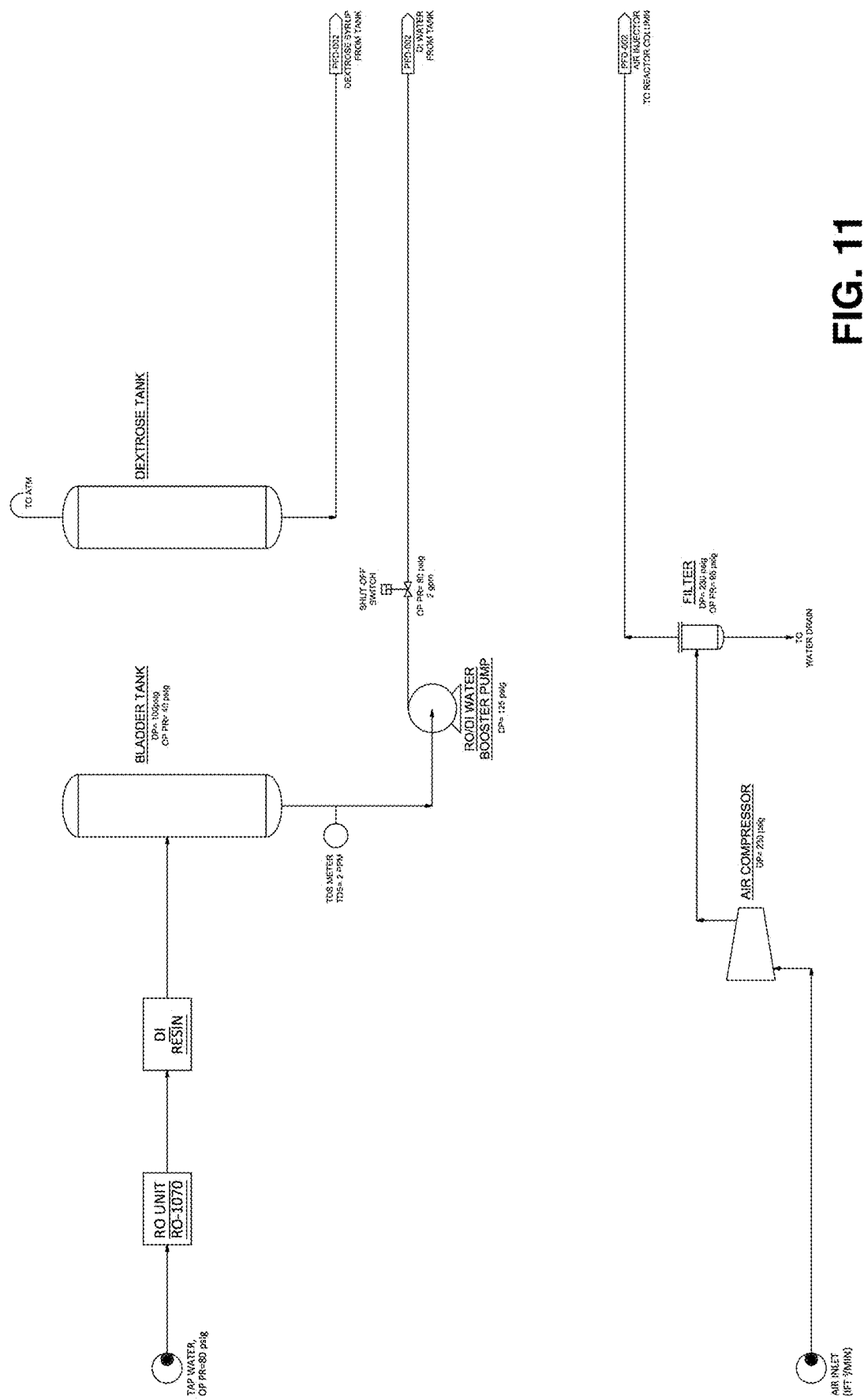
FIG. 11 illustrates an overview schematic diagram for another non-limiting of the HGA production method and system of the disclosure described herein.

FIG. 11 illustrates an overview schematic diagram for another non-limiting of the HGA production method and system of the disclosure described herein. Here, a water source (BLADDER TANK) may also be filled or sourced from tap water which is directed to a Reverse Osmosis Unit (RO UNIT) and a Deionization Resin (DI RESIN) prior to entering the water source. In addition, an air filter may be provided to purify the compressed gas or oxygen prior to it entering the reaction chamber.

Figure 12A:
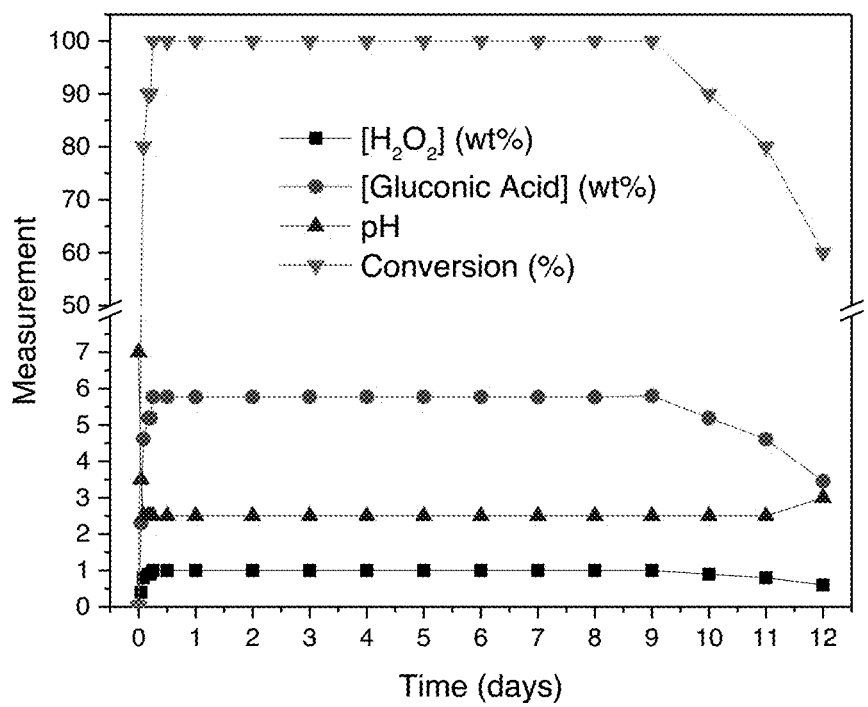
FIGS. 12A-12C illustrate line graph data charts of sample experimental data for one exemplary test and run of the HGA production method and system of the disclosure described herein.
Figure 12B:
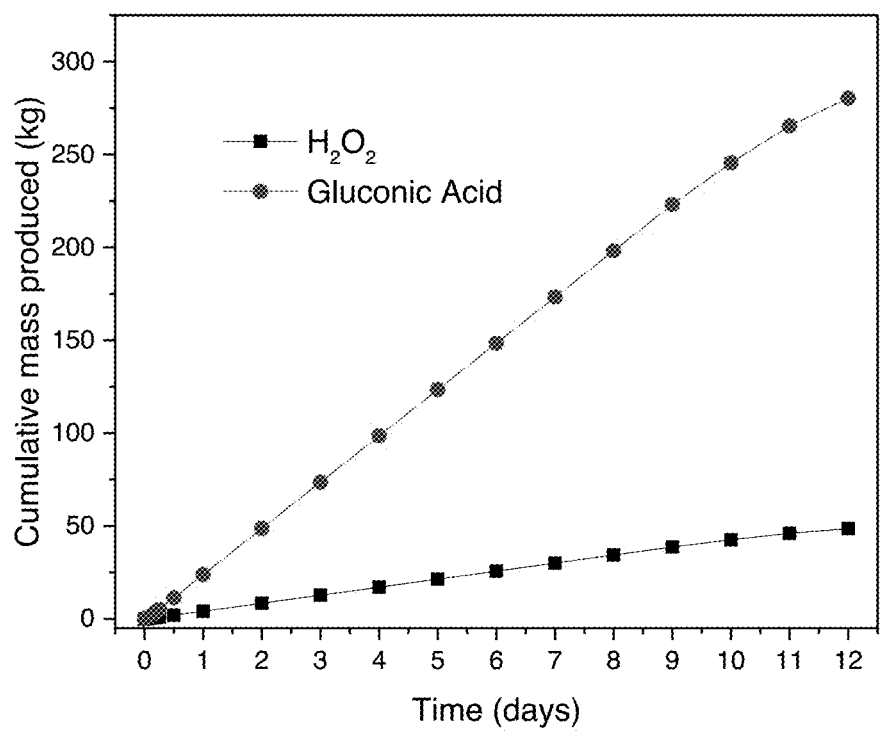
Figure 12C:
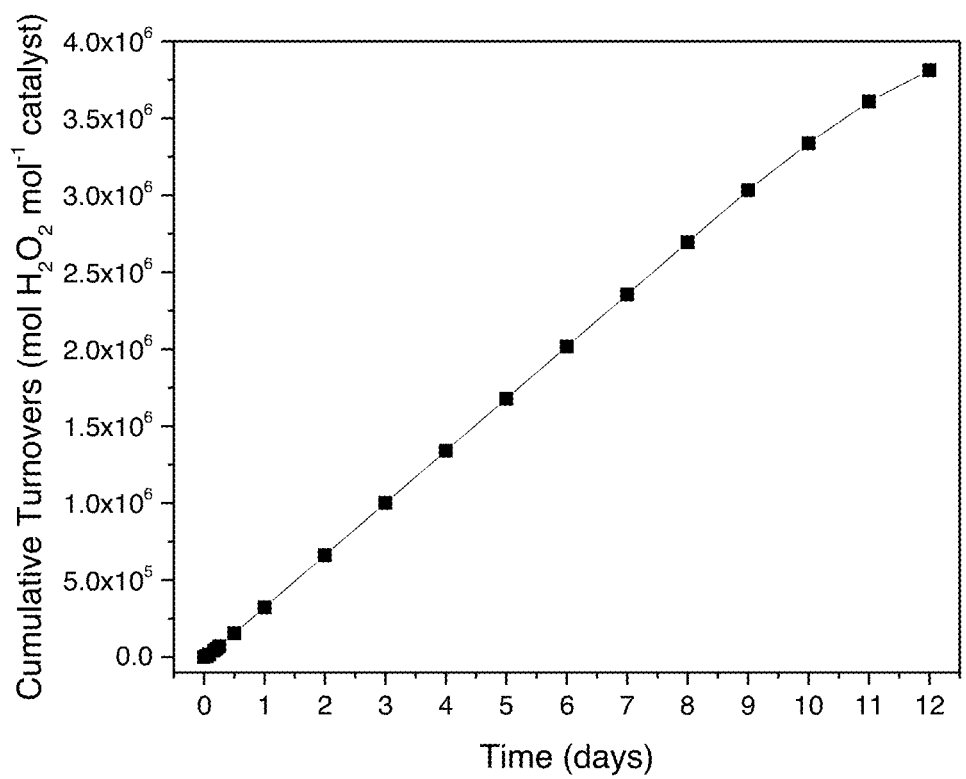

FIGS. 12A-12C illustrate line graph data charts of sample experimental data for one exemplary test and run of the HGA production method and system of the disclosure described herein. Here, the testing conditions for HGA production method and system, and more specifically the reaction chamber, were such that the experimental test and run was conducted over 12 days, the average reactor pressure was at 75 psig, temperature was ambient temperature, air flowrate was at 3 scfm, catalyst mass load was at 60 g, inlet dextrose concentration was at 5.3% wt. in deionized water, average residence time was 90 minutes, inlet and outlet liquid flowrates were at 300 mL/min, operation mode was set as continuous, and the initial reactor charge was catalyst in 5.3% wt. dextrose solution. The results of this exemplary test run of the HGA production method and system is shown with respect to FIGS. 12A-12C. In particular, FIG. 12A illustrates the measured amount of hydrogen peroxide and gluconic acid produced in the working and final solution, the pH of the working and final solution, and the conversion rate over the 12-day experimental run. In addition, FIG. 12B also illustrates the cumulative mass produced of hydrogen peroxide and gluconic acid working and final solution over the 12-day experimental run. Further, FIG. 12C illustrates the rate of cumulative turnovers over the 12-day experimental run.

It is contemplated within the scope of the disclosure described herein that hydrogen peroxide and gluconic acid concentration levels in excess of 10% wt. may be produced using the one or more embodiment disclosed herein. In addition, any of the aforementioned production systems and methods with respect to FIGS. 1A-10B may be as part of a small to medium or medium to large-scale production plant. Alternatively, the productions systems of FIGS. 1-11 may also be a portable or mobile hydrogen production system that can have individual modular components or be a part of one single unit.

From the foregoing it will be seen that the disclosure described herein is one well adapted to attain all ends and objectives herein-above set forth, together with the other advantages which are obvious and which are inherent to the disclosure described herein. Since many possible embodiments may be made of the disclosure described herein without departing from the scope thereof, it is to be understood that all matters herein set forth or shown in the accompanying drawings are to be interpreted as illustrative, and not in a limiting sense. While specific embodiments have been shown and discussed, various modifications may of course be made, and the disclosure described herein is not limited to the specific forms or arrangement of parts described herein, except insofar as such limitations are included in the following claims. Further, it will be understood that certain features and sub-combinations are of utility and may be employed without reference to other features and sub-combinations.

What is claimed is:

1. A hydrogen peroxide and gluconic acid production method, comprising:
  receiving an aqueous solution, wherein the aqueous solution is comprised of an organic material, water, and an enzyme;
  receiving the aqueous solution at a reaction chamber comprised of a bubble column reactor, wherein the reaction chamber further comprises an enzymatic reaction between a vapor phase and a liquid phase, and wherein the enzymatic reaction produces a first solution comprising produced hydrogen peroxide and produced gluconic acid as a result of the enzymatic reaction and the enzyme;
  receiving the first solution at a separation chamber after the reaction chamber, wherein the separation chamber is comprised of a semi-permeable membrane having a pre-defined molecular weight barrier adapted to prevent the enzyme from permeating therethrough;
  circulating the first solution through the semi-permeable membrane of the separation chamber, wherein the circulating results in a second solution, and wherein the second solution is comprised of the produced hydrogen peroxide and produced gluconic acid; and receiving the second solution at a collection chamber after the separation chamber.

2. The hydrogen peroxide and gluconic acid production method of claim 1, wherein the organic material is comprised of glucose.

3. The hydrogen peroxide and gluconic acid production method of claim 1, wherein the organic material is comprised of dextrose syrup.

4. The hydrogen peroxide and gluconic acid production method of claim 1, wherein the enzyme is comprised of glucose oxidase.

5. The hydrogen peroxide and gluconic acid production method of claim 4, wherein the glucose oxidase is free or immobilized within the reaction chamber.

6. The hydrogen peroxide and gluconic acid production method of claim 1, wherein the semi-permeable membrane comprises a vertical shell-and-tube configuration.

7. The hydrogen peroxide and gluconic acid production method of claim 1, wherein the pre-defined molecular weight barrier of the semi-permeable membrane is at least 1,000 Daltons.

8. The hydrogen peroxide and gluconic acid production method of claim 1, further comprising receiving air bubbles from the reaction chamber at a defoamer or anti-foaming agent component.

9. The hydrogen peroxide and gluconic acid production method of claim 8, wherein the defoamer further comprises a vapor-liquid separator.

10. The hydrogen peroxide and gluconic acid production method of claim 9, receiving the separated liquid from the vapor-liquid separator at the reaction chamber.

11. The hydrogen peroxide and gluconic acid production method of claim 1, wherein the second solution comprises at least 0.1% wt. hydrogen peroxide and at least 0.1% wt. gluconic acid.

12. The hydrogen peroxide and gluconic acid production method of claim 1, wherein the aqueous solution or the second solution further comprises one or more additives or stabilizers comprised of one or more of: gluconic acid, sodium gluconate, urea, sodium stannate, and silver nitrate.

13. The hydrogen peroxide and gluconic acid production method of claim 1, further comprising at least partially converting the gluconic acid into gluconate salts.

14. The hydrogen peroxide and gluconic acid production method of claim 1, further comprising converting the second solution into a third solution, wherein the third solution is comprised of solid gluconic acid or solid gluconate salts.

15. The hydrogen peroxide and gluconic acid production method of claim 14, further comprising converting the third solution into a fourth solution, wherein the fourth solution is comprised of a mixture of gaseous hydrogen peroxide and water.

16. The hydrogen peroxide and gluconic acid production method of claim 15, further comprising separating the fourth solution into a fifth solution and sixth solution via a distillation column, wherein the fifth solution is comprised of hydrogen peroxide and water at a bottom region of the distillation column and the sixth solution is comprised of pure water from a top region of the distillation column.

17. A hydrogen peroxide and gluconic acid production method, comprising:
receiving an aqueous solution, wherein the aqueous solution is comprised of glucose, purified water, and glucose oxidase enzyme;
receiving the aqueous solution at a vertical bubble column reaction chamber;
delivering gas at a pre-defined pressure into the vertical bubble column reaction chamber, wherein the reaction chamber comprises an enzymatic reaction further comprised of a gas phase and a liquid phase, and wherein the enzymatic reaction produces a first solution comprising produced hydrogen peroxide and produced gluconic acid as a result of the enzymatic reaction and the glucose oxidase enzyme;
receiving the first solution at a membrane separation chamber after the reaction chamber, wherein the separation chamber is comprised of a semi-permeable membrane having a pre-defined molecular weight barrier;
circulating the first solution through the membrane separation chamber, wherein the circulating results in a second solution, and wherein the second solution is comprised of the produced hydrogen peroxide and produced gluconic acid;
receiving residual air bubbles from the reaction chamber at an air and liquid separation chamber; and
separating the air and liquid from the residual air bubbles at the air and liquid separation chamber, and diverting the separated liquid into the reaction chamber.

18. A hydrogen peroxide and organic compound production method, comprising:
receiving an aqueous solution, wherein the aqueous solution is comprised of an organic material, water, and an enzyme;
receiving the aqueous solution at a reaction chamber, wherein the reaction chamber comprises an enzymatic reaction between a vapor phase and a liquid phase, wherein the enzymatic reaction results in a first solution comprising produced hydrogen peroxide as a result of the enzymatic reaction, an organic compound, and the enzyme;
receiving the first solution at a separation chamber after the reaction chamber, wherein the separation chamber is comprised of a semi-permeable membrane having a pre-defined molecular weight barrier; and
circulating the first solution through the semi-permeable membrane of the separation chamber, wherein the circulating results in a second solution, and wherein the second solution is comprised of the produced hydrogen peroxide and the organic compound without the enzyme or no more than 100 ppm of the enzyme.

* * * * *